US 8,021,398 B2

(12) United States Patent
Sweeney et al.

(10) Patent No.: US 8,021,398 B2
(45) Date of Patent: Sep. 20, 2011

(54) SPINAL FIXATION SYSTEM

(75) Inventors: Patrick J. Sweeney, Flossmoor, IL (US); Michael S. Butler, Fishers, IN (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 958 days.

(21) Appl. No.: 11/461,987

(22) Filed: Aug. 2, 2006

(65) Prior Publication Data

US 2007/0055239 A1 Mar. 8, 2007

Related U.S. Application Data

(63) Continuation-in-part of application No. 11/071,604, filed on Mar. 3, 2005, which is a continuation-in-part of application No. 10/864,673, filed on Jun. 9, 2004.

(60) Provisional application No. 60/705,580, filed on Aug. 4, 2005.

(51) Int. Cl.
 *A61B 17/70* (2006.01)
(52) U.S. Cl. .................. 606/269; 606/268; 606/272
(58) Field of Classification Search ............ 606/60, 606/246, 250–279, 300–321; 403/84, 97
See application file for complete search history.

(56) References Cited

U.S. PATENT DOCUMENTS

| 2,414,882 | A | 1/1947 | Longfellow |
| 3,289,290 | A | 12/1966 | Sandor |
| 4,399,814 | A | 8/1983 | Pratt, Jr. et al. |
| 4,648,388 | A | 3/1987 | Steffee |
| 4,653,489 | A | 3/1987 | Tronzo |
| 4,790,297 | A | 12/1988 | Luque |
| 4,805,602 | A | 2/1989 | Puno et al. |
| 4,863,472 | A | 9/1989 | Tormala et al. |
| 5,047,029 | A * | 9/1991 | Aebi et al. ............. 606/264 |
| 5,092,893 | A | 3/1992 | Smith |
| 5,098,435 | A | 3/1992 | Stednitz et al. |
| 5,129,899 | A | 7/1992 | Small et al. |
| 5,190,543 | A | 3/1993 | Schlapfer |
| 5,261,909 | A * | 11/1993 | Sutterlin et al. ......... 606/264 |

(Continued)

FOREIGN PATENT DOCUMENTS

DE 92 15 561 1/1993

(Continued)

OTHER PUBLICATIONS

Lamendola, Mark, "How to Use Belleville Washers Correctly," Dec. 1, 1997, EC&M, 2 pages.
Chen, Pei-Yu et al., "Closed Reduction With Intramedullary Fixation for Midclavicular Fractures," Orthopedics journal, May 2004, pp. 459-462, vol. 27, No. 5.
"The Trio® Spinal System," printed Feb. 9, 2005, 2 pages.

(Continued)

*Primary Examiner* — Eduardo C Robert
*Assistant Examiner* — Jerry Cumberledge
(74) *Attorney, Agent, or Firm* — Foley & Lardner LLP

(57) ABSTRACT

According to one embodiment of the invention, a spinal fixation system includes a bone screw having a longitudinal access and a fixation rod configured to connect the bone screw to at least one additional bone screw. The fixation rod is lateral to the longitudinal axis. A coupling mechanism includes a bone screw securing device configured to secure the coupling mechanism to the bone screw and a fixation rod securing device configured to secure the coupling mechanism to the fixation rod. The spinal fixation system further includes a fastening mechanism. Rotation of the fastening mechanism secures the bone screw securing device to the bone screw and the fixation rod securing device to the fixation rod.

16 Claims, 18 Drawing Sheets

U.S. PATENT DOCUMENTS

| | | | |
|---|---|---|---|
| 5,350,380 A | | 9/1994 | Goble et al. |
| 5,352,226 A * | | 10/1994 | Lin .................. 606/264 |
| 5,423,819 A | | 6/1995 | Small et al. |
| 5,449,257 A | | 9/1995 | Giannuzzi |
| 5,501,684 A | | 3/1996 | Schlapfer et al. |
| 5,545,163 A | | 8/1996 | Miller et al. |
| 5,562,661 A * | | 10/1996 | Yoshimi et al. ........... 606/264 |
| 5,569,252 A | | 10/1996 | Justin et al. |
| 5,582,612 A | | 12/1996 | Lin |
| 5,584,833 A | | 12/1996 | Fournet-Fayard et al. |
| 5,611,800 A * | | 3/1997 | Davis et al. .................. 606/250 |
| 5,613,968 A | | 3/1997 | Lin |
| 5,643,262 A * | | 7/1997 | Metz-Stavenhagen et al. ....................... 606/261 |
| 5,643,263 A * | | 7/1997 | Simonson ................. 606/278 |
| 5,645,547 A | | 7/1997 | Coleman |
| 5,649,931 A | | 7/1997 | Bryant et al. |
| 5,667,513 A | | 9/1997 | Torrie et al. |
| 5,688,272 A | | 11/1997 | Montague et al. |
| 5,688,275 A * | | 11/1997 | Koros et al. ................ 606/264 |
| 5,885,285 A * | | 3/1999 | Simonson .................. 606/278 |
| 5,938,663 A * | | 8/1999 | Petreto ....................... 606/278 |
| 5,947,967 A | | 9/1999 | Barker |
| 5,976,135 A | | 11/1999 | Sherman et al. |
| 6,001,098 A * | | 12/1999 | Metz-Stavenhagen et al. ....................... 606/264 |
| 6,030,388 A | | 2/2000 | Yoshimi et al. |
| 6,033,406 A | | 3/2000 | Mathews |
| 6,045,555 A | | 4/2000 | Smith et al. |
| 6,048,343 A | | 4/2000 | Mathis et al. |
| 6,059,785 A | | 5/2000 | Schavan et al. |
| 6,063,089 A | | 5/2000 | Errico et al. |
| 6,063,090 A * | | 5/2000 | Schlapfer ................... 606/270 |
| 6,086,588 A | | 7/2000 | Ameil et al. |
| 6,096,060 A | | 8/2000 | Fitts et al. |
| 6,111,164 A | | 8/2000 | Rainey et al. |
| 6,123,706 A * | | 9/2000 | Lange ........................ 606/264 |
| 6,139,549 A | | 10/2000 | Keller |
| 6,146,383 A | | 11/2000 | Studer et al. |
| 6,159,210 A | | 12/2000 | Voor |
| 6,179,838 B1 | | 1/2001 | Fiz |
| 6,183,473 B1 * | | 2/2001 | Ashman ..................... 606/278 |
| 6,187,005 B1 | | 2/2001 | Brace et al. |
| 6,210,376 B1 | | 4/2001 | Grayson |
| 6,210,413 B1 * | | 4/2001 | Justis et al. ................. 606/254 |
| 6,231,575 B1 * | | 5/2001 | Krag .......................... 606/264 |
| 6,248,104 B1 * | | 6/2001 | Chopin et al. .............. 606/267 |
| 6,248,105 B1 | | 6/2001 | Schlapfer et al. |
| 6,248,107 B1 * | | 6/2001 | Foley et al. ................. 606/264 |
| 6,254,602 B1 | | 7/2001 | Justis |
| 6,315,779 B1 | | 11/2001 | Morrison et al. |
| 6,317,957 B1 | | 11/2001 | Gregor et al. |
| 6,355,039 B1 | | 3/2002 | Troussel et al. |
| 6,371,957 B1 | | 4/2002 | Amrein et al. |
| 6,379,357 B1 | | 4/2002 | Bernstein et al. |
| 6,402,749 B1 | | 6/2002 | Ashman |
| 6,471,703 B1 | | 10/2002 | Ashman |
| 6,482,207 B1 | | 11/2002 | Errico |
| 6,520,962 B1 * | | 2/2003 | Taylor et al. ............... 606/278 |
| 6,582,436 B2 | | 6/2003 | Schlapfer et al. |
| 6,613,050 B1 | | 9/2003 | Wagner et al. |
| 6,616,665 B2 | | 9/2003 | Grafton et al. |
| 6,626,906 B1 * | | 9/2003 | Young ........................ 606/278 |
| 6,641,583 B2 | | 11/2003 | Shluzas et al. |
| 6,641,586 B2 | | 11/2003 | Varieur |
| 6,648,887 B2 * | | 11/2003 | Ashman ..................... 606/278 |
| 6,648,894 B2 | | 11/2003 | Abdelgany et al. |
| 6,663,642 B2 | | 12/2003 | Beyar et al. |
| 6,668,688 B2 | | 12/2003 | Zhao et al. |
| 6,676,661 B1 * | | 1/2004 | Martin Benlloch et al. ... 606/264 |
| 6,685,705 B1 * | | 2/2004 | Taylor ........................ 606/278 |
| 6,695,846 B2 | | 2/2004 | Richelsoph et al. |
| 6,706,045 B2 | | 3/2004 | Lin et al. |
| 6,723,100 B2 | | 4/2004 | Biedermann et al. |
| 6,755,835 B2 | | 6/2004 | Schultheiss et al. |
| 6,786,907 B2 | | 9/2004 | Lange |
| 6,827,722 B1 | | 12/2004 | Schoenefeld |
| 6,832,999 B2 | | 12/2004 | Ueyama et al. |
| 6,835,196 B2 * | | 12/2004 | Biedermann et al. ......... 606/308 |
| 6,858,030 B2 | | 2/2005 | Martin et al. |
| 6,887,242 B2 | | 5/2005 | Doubler et al. |
| 6,893,444 B2 | | 5/2005 | Orbay |
| 6,899,714 B2 | | 5/2005 | Vaughan |
| 6,945,972 B2 | | 9/2005 | Frigg et al. |
| 6,947,967 B2 * | | 9/2005 | Ferris et al. .................. 709/203 |
| 6,949,100 B1 | | 9/2005 | Venturini |
| 6,951,561 B2 | | 10/2005 | Warren et al. |
| 7,022,122 B2 | | 4/2006 | Amrein et al. |
| 7,575,587 B2 * | | 8/2009 | Rezach et al. ............... 606/278 |
| 7,604,643 B2 | | 10/2009 | Ciccone et al. |
| 7,744,635 B2 | | 6/2010 | Sweeney et al. |
| 2002/0045899 A1 | | 4/2002 | Errico et al. |
| 2002/0143332 A1 | | 10/2002 | Lin et al. |
| 2002/0143341 A1 | | 10/2002 | Biedermann et al. |
| 2002/0169450 A1 | | 11/2002 | Lange |
| 2002/0183748 A1 | | 12/2002 | Martin et al. |
| 2003/0000350 A1 | | 1/2003 | Zhao et al. |
| 2003/0023240 A1 | | 1/2003 | Amrein et al. |
| 2003/0045878 A1 * | | 3/2003 | Petit et al. .................... 606/61 |
| 2003/0073997 A1 | | 4/2003 | Doubler et al. |
| 2003/0105460 A1 * | | 6/2003 | Crandall et al. ............. 606/61 |
| 2003/0149431 A1 | | 8/2003 | Varieur |
| 2003/0149432 A1 | | 8/2003 | Frigg et al. |
| 2003/0171751 A1 | | 9/2003 | Ritland |
| 2003/0176864 A1 * | | 9/2003 | Ueyama et al. ............. 606/61 |
| 2003/0191473 A1 * | | 10/2003 | Taylor ......................... 606/61 |
| 2003/0208202 A1 | | 11/2003 | Falahee |
| 2004/0010253 A1 * | | 1/2004 | Morrison ..................... 606/61 |
| 2004/0092930 A1 | | 5/2004 | Petit et al. |
| 2004/0102780 A1 | | 5/2004 | West, Jr. |
| 2004/0147928 A1 * | | 7/2004 | Landry et al. ............... 606/61 |
| 2004/0181226 A1 | | 9/2004 | Michelson |
| 2004/0215190 A1 | | 10/2004 | Nguyen et al. |
| 2004/0236330 A1 | | 11/2004 | Purcell et al. |
| 2004/0243139 A1 | | 12/2004 | Lewis et al. |
| 2004/0254574 A1 | | 12/2004 | Morrison et al. |
| 2005/0070901 A1 | | 3/2005 | David |
| 2005/0113830 A1 * | | 5/2005 | Rezach et al. ................ 606/60 |
| 2005/0113833 A1 | | 5/2005 | Davison |
| 2005/0277923 A1 | | 12/2005 | Sweeney |
| 2006/0079903 A1 | | 4/2006 | Wong |
| 2006/0089647 A1 | | 4/2006 | Culbert et al. |
| 2006/0149234 A1 * | | 7/2006 | de Coninck .................. 606/61 |
| 2006/0149245 A1 | | 7/2006 | Sweeney |
| 2006/0195096 A1 * | | 8/2006 | Lee et al. ..................... 606/61 |
| 2007/0118122 A1 | | 5/2007 | Butler et al. |
| 2007/0173833 A1 * | | 7/2007 | Butler et al. ................. 606/61 |
| 2011/0004251 A1 | | 1/2011 | Sweeney et al. |

FOREIGN PATENT DOCUMENTS

| | | |
|---|---|---|
| WO | WO 02/36026   * | 5/2002 |
| WO | WO 02/36026 A2 | 5/2002 |
| WO | WO 03/028538 A2 | 4/2003 |
| WO | WO-2005/122965 | 12/2005 |
| WO | WO-2007/019204 | 2/2007 |

OTHER PUBLICATIONS

International Search Report and Written Opinion for Application No. PCT/US05/20157, date of mailing Jan. 6, 2006, 8 pages.

Office Action for U.S. Appl. No. 11/349,763, mail date Nov. 3, 2009, 8 pages.

Notice of Allowance for U.S. Appl. No. 11/071,604, mail date Feb. 22, 2010, 9 pages.

Office Action for U.S. Appl. No. 11/349,763, mail date Apr. 30, 2010, 10 pages.

European Patent Office Communication pursuant to Article 93(3) EPC for Application No. 05 757 401.4, date of mailing, Nov. 5, 2009 (6 pgs.).

International Search Report and Written Opinion for International Application No. PCT/US2006/030187, date of completion Jun. 20, 2007, 6 pages.

Notice of Allowance for U.S. Appl. No. 10/864,673, mail date Feb. 18, 2011, 12 pages.

* cited by examiner

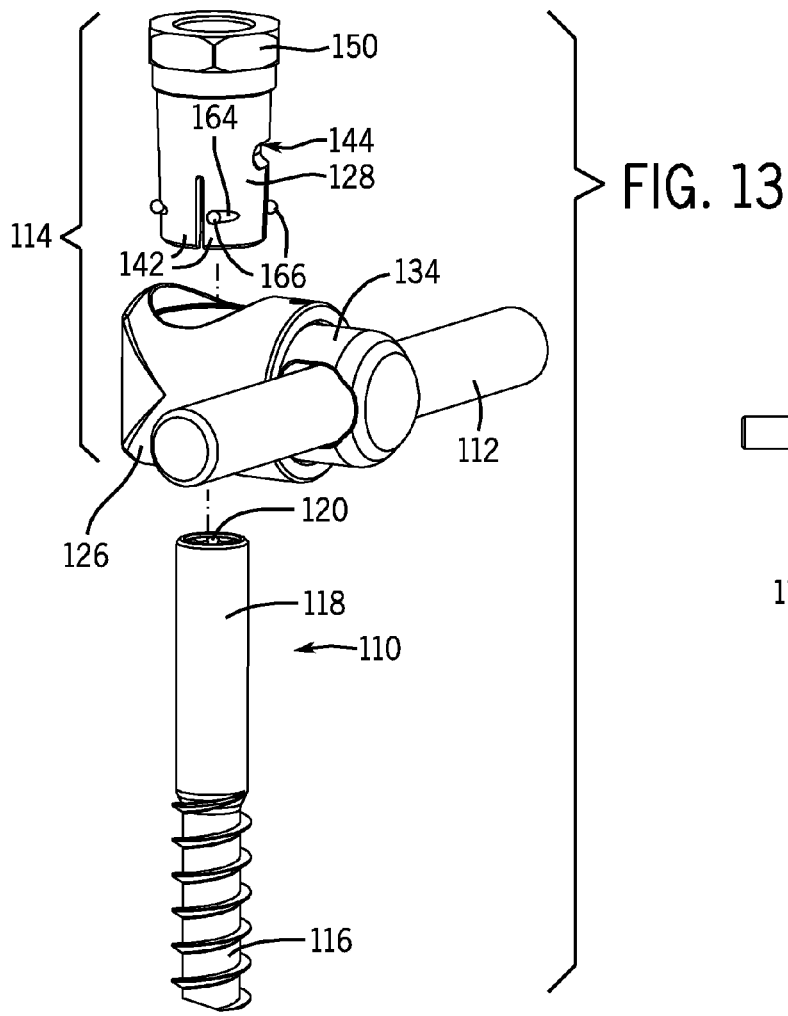
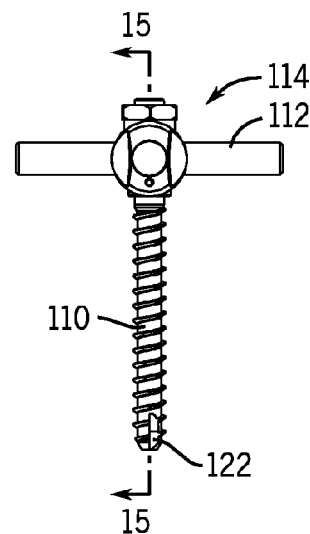
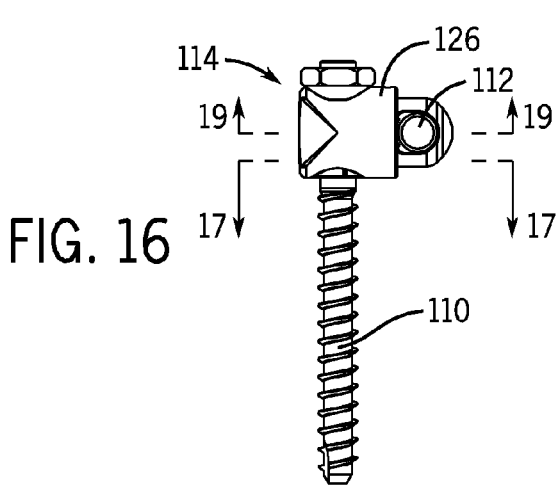
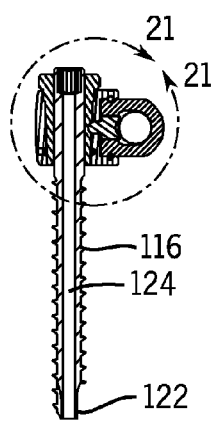
FIG. 13
FIG. 14
FIG. 15
FIG. 16

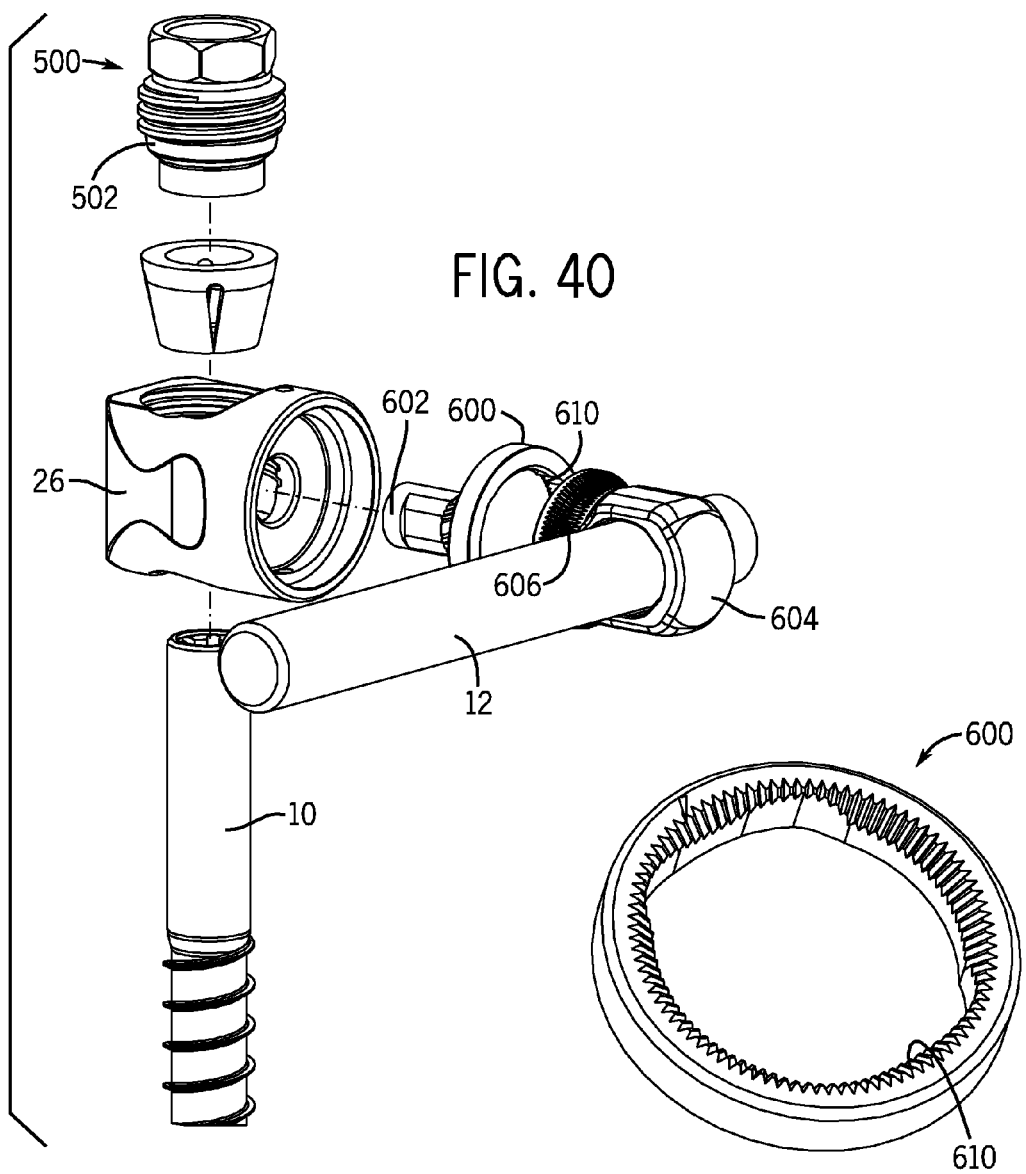
FIG. 40
FIG. 41
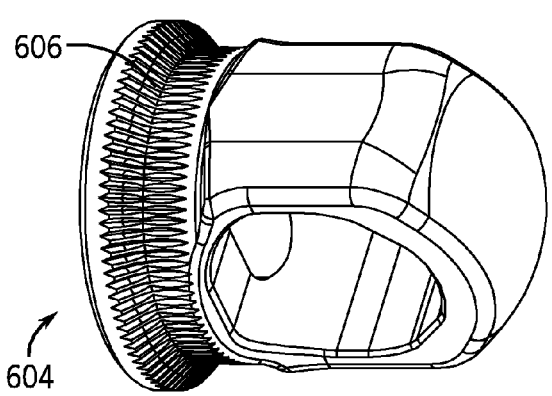
FIG. 42

SPINAL FIXATION SYSTEM

This application claims the benefit of U.S. Provisional Application No. 60/705,580, filed Aug. 4, 2005, which is incorporated by reference herein. This application is a continuation-in-part of U.S. application Ser. No. 11/071,604, filed Mar. 3, 2005, which is a continuation-in-part of application Ser. No. 10/864,673, filed Jun. 9, 2004, both of which are incorporated by reference herein.

FIELD OF THE INVENTION

The present invention relates to instrumentation and methods used in the performance of spinal fusion procedures. In particular, the present invention relates to a spinal fixation system and related surgical methods.

BACKGROUND OF THE INVENTION

The spinal column is comprised of twenty-six interlocking vertebrae. The vertebrae are separated by disks. The spine provides load-bearing support for one-half of the body's mass and it protects the nerves of the spinal column. The disks provide shock absorption and facilitate the bending of the spine.

The combination of the vertebrae and disks at each vertebral segment allows for motion of the spine, in particular, flexing, rotation, and extension. The motion and support functions of the spine, in combination with the many interlocking parts and nerve roots associated with the spinal column can result in back pain due to various reasons. Such back pain may result from the degeneration of disks due to age, disease, or injury. Further, vertebral bodies may be compromised due to disease or defect, such as a tumor, or injury, such as fracture.

Spinal fusion or fixation surgery is one way to treat back pain. Further, spinal fusion or fixation may be used to correct an abnormal curvature of the spine or stabilize the spine due to injury or disease affecting one or more disks or vertebrae. In a spinal fusion procedure, two or more adjacent vertebrae in the spine are fused together. The fusion is typically accomplished by the utilization of spinal instrumentation including pedicle screws and associated rods or plates used to mechanically fix the vertebrae together. Pedicle screws are typically used in spinal fusion surgery because the pedicle serves as a strong mechanical attachment point to the spine. Bone graft material may be utilized to aid in the creation of bone structure between the fused vertebrae to create a single bone.

Spinal fixation components vary depending on the system being utilized but typically include pedicle screws that are inserted through the pedicle and into the vertebral body. The pedicle screws are typically attached to one another by a linking device, such as a rod or plate, that extends vertically along the row of pedicle screws that are inserted. Several coupling systems are known in the art that are used for coupling the pedicle screws to the linking device, which is oriented parallel to the spinal column. Typically two columns of pedicle screws and linking devices are used, one on each side of the spinal column. After installation, the two linking devices may be attached to one another to provide additional stabilization of that portion of the spine. As an alternative or in addition to pedicle screws, spinal hooks may be used, each spinal hook being coupled to a vertebra via a portion of the vertebral arch.

Because of anatomical variations, the pedicle screws that are fixed to one another in a spinal fusion procedure may not be in longitudinal alignment with one another. Accordingly, spinal fixation systems, whether utilizing a rod or a plate, strive to allow some variability in the placement of the pedicle screws while still accomplishing the goal of fixation with a single rod or plate along the pedicle screws.

One challenge associated with the design of a spinal fixation system is the connection between the pedicle screws and the linking device. Ideally, the number of components involved should be minimized, especially the number of components that must be threaded together (such as nuts and rods) in order to ease the assembly process and minimize the overall time of the surgical procedure.

There is also a need for a spinal fixation system that may be utilized with a minimally invasive surgical approach, such as one that utilizes smaller access apertures or ports rather than a large incision along the entire portion of the spine being treated. A spinal fixation system that addresses the need for a minimally invasive approach may also address the desire to utilize bone graft material along the fixation site to enhance bony in-growth.

Further, there is a need for a spinal fixation system that not only utilizes fewer components but that requires fewer steps for assembly onto the spine, thus shortening the overall time of the surgical procedure.

It would be desirable to provide a system and/or method that provides one or more of these or other advantageous features or addresses one or more of the above-identified needs. Other features and advantages will be made apparent from the present specification. The teachings disclosed extend to those embodiments that fall within the scope of the claims, regardless of whether they accomplish one or more of the aforementioned needs.

SUMMARY OF THE INVENTION

The invention relates to a spinal fixation system having a bone screw with a longitudinal axis and a fixation rod configured to connect the bone screw to at least one additional bone screw. The fixation rod is lateral to the longitudinal axis. A coupling mechanism includes a bone screw securing device configured to secure the coupling mechanism to the bone screw and a fixation rod securing device configured to secure the coupling mechanism to the fixation rod. The spinal fixation system further includes a fastening mechanism. Rotation of the fastening mechanism secures the bone screw securing device to the bone screw and the fixation rod securing device to the fixation rod.

The invention further relates to a spinal fixation system having a screw, a body received on the screw, a collet received on the screw, and a nut received on the screw and secured to the body. The spinal fixation system further includes fixation rod holder coupled to the body and a pin slidably coupled to the body and the fixation rod holder. The nut operatively engages the pin to secure the fixation rod holder to a fixation rod and operatively engages the collet to secure the collet to the screw.

The invention further relates to a bone screw and fixation rod coupling mechanism for a spinal fixation system having a bone screw securing device configured to secure the coupling mechanism to a bone screw and a fixation rod securing device configured to secure the coupling mechanism to a fixation rod. The fixation rod securing device includes a rod holder having a plurality of teeth and a retaining ring coupled to the rod holder, the retaining ring having a plurality of teeth. The plurality of teeth on the retaining ring interlock with the plurality of teeth on the rod holder to prevent rotation of the rod holder relative to the retaining ring.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which:

FIG. 13 is a partial exploded perspective view of a spinal fixation system according to a second embodiment of the invention;

FIG. 14 is a front elevation view of the spinal fixation system of FIG. 13;

FIG. 15 is a sectional view of the spinal fixation system of FIG. 13 taken generally along line 15-15 of FIG. 14;

FIG. 16 is a side elevation view of the spinal fixation system of FIG. 13;

FIG. 40 is a partial exploded perspective view of a spinal fixation system according to a seventh embodiment of the invention;

FIG. 41 is a perspective view of a retaining ring of the spinal fixation system of FIG. 40;

FIG. 42 is a perspective view of a the rod holder of the spinal fixation system of FIG. 40;

DESCRIPTION OF PREFERRED EMBODIMENTS

Figure 1:
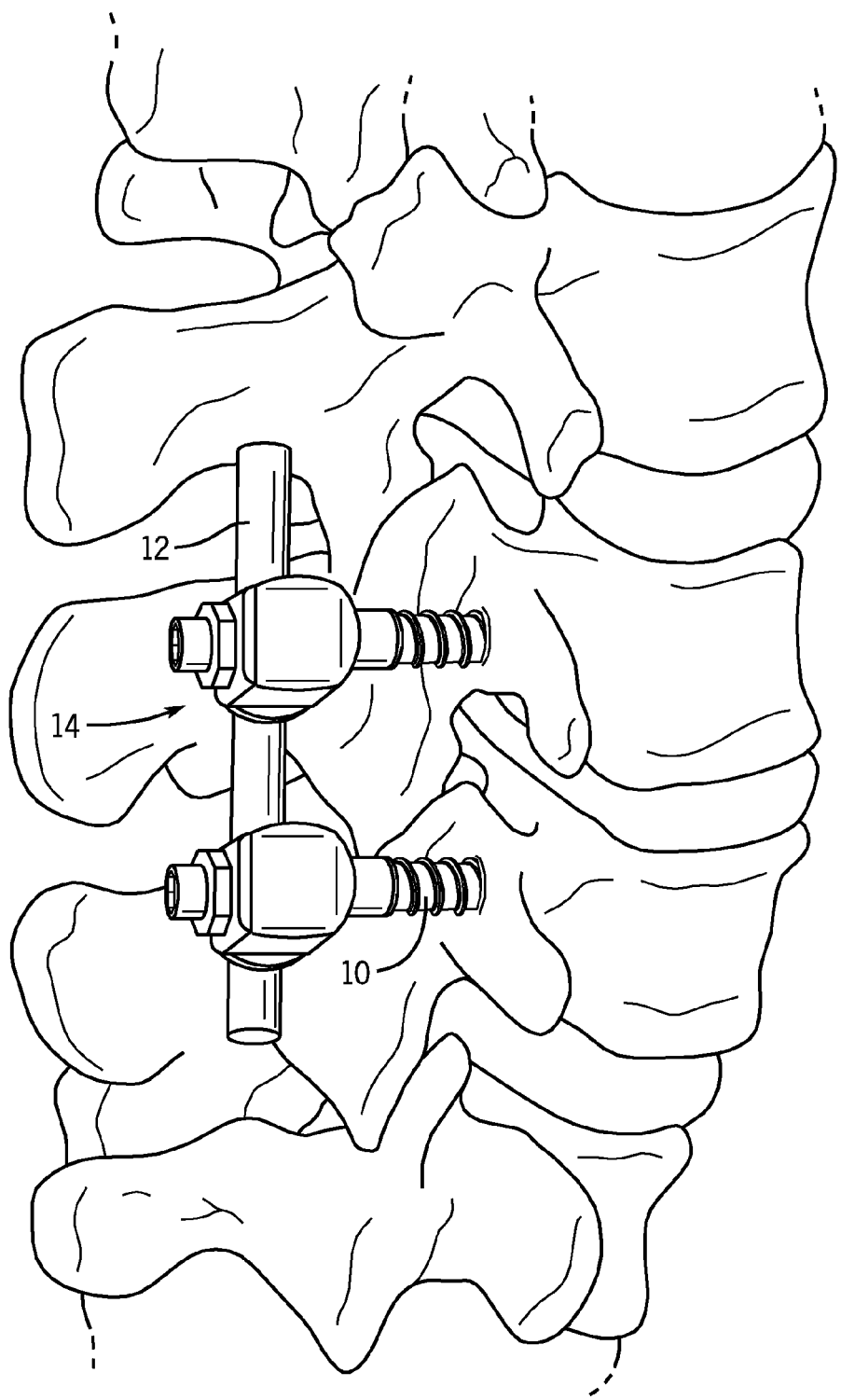
FIG. 1 is a perspective view of a spinal fixation system connected to a spine.

Referring to FIG. 1, a spinal fixation system according to an exemplary embodiment of the invention includes a bone coupling element or bone screw, shown as pedicle screw 10, a linking device or fixation element, shown as fixation rod 12, and a coupling mechanism, generally shown as coupling mechanism 14. The pedicle screw 10 is coupled to the fixation rod 12 via the coupling mechanism 14. In use, the pedicle screw 10 may be inserted through a pedicle and into a vertebra and linked to other pedicle screws by the fixation rod 12. The length of the fixation rod 12 is chosen to accommodate the total distance along the pedicle screws that are linked together.

Figure 2:
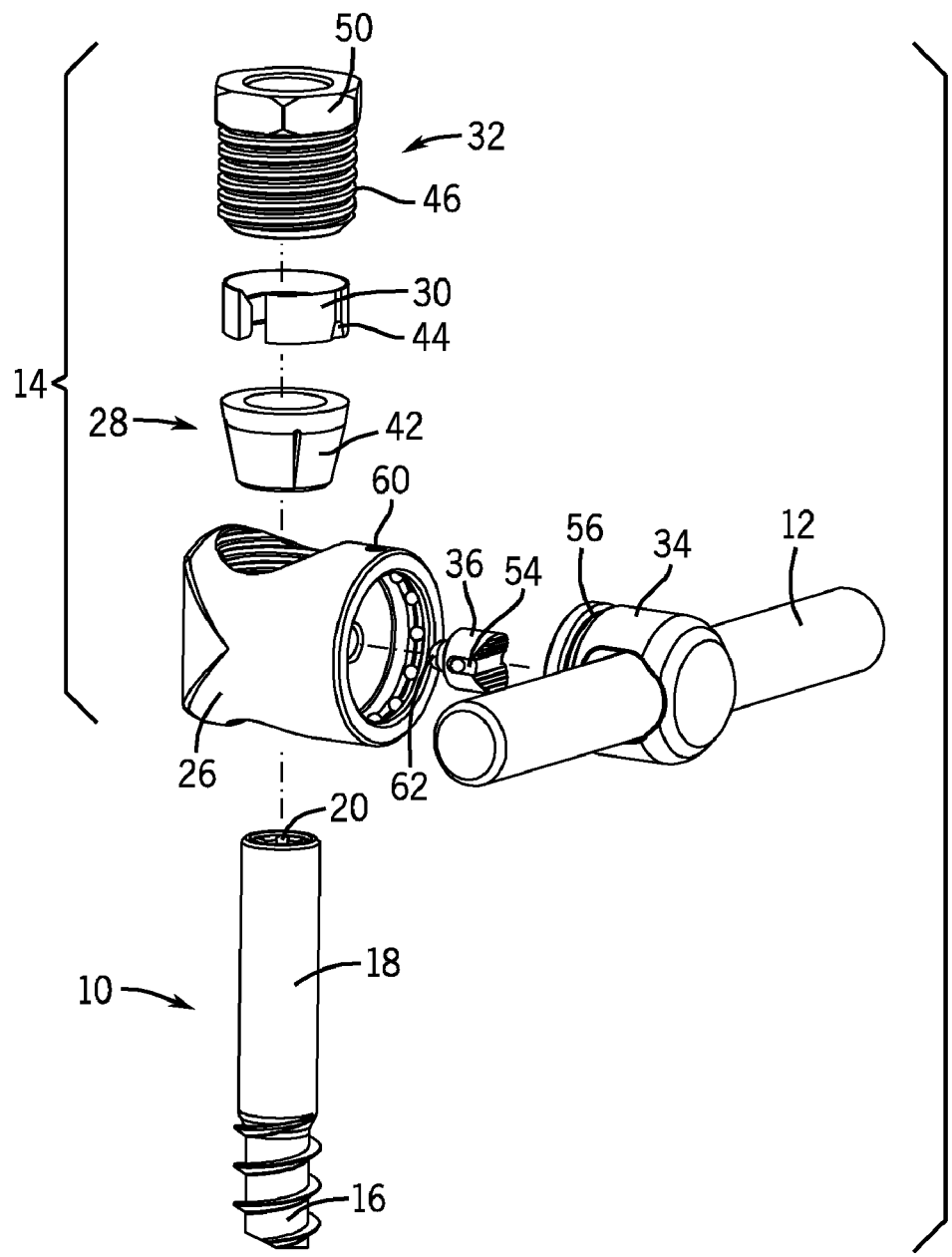
FIG. 2 is an partial exploded perspective view of a spinal fixation system.
Figure 3:
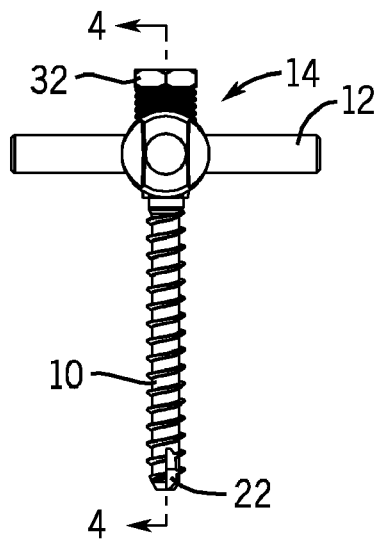
FIG. 3 is a front elevation view of the spinal fixation system of FIG. 2.
Figure 4:
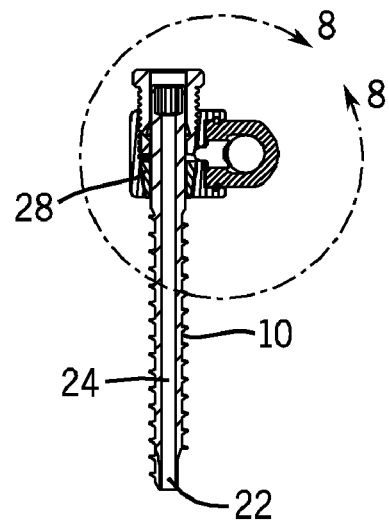
FIG. 4 is a sectional view of the spinal fixation system of FIG. 2 taken generally along line 4-4 of FIG. 3.

Referring to the embodiment of FIGS. 2-12, the pedicle screw 10 includes a threaded portion 16 and a non-threaded upper portion, shown as post 18. At the top of the post 18, an engagement mechanism for a screwdriver or power drill, shown as recess 20, may be utilized. Referring to FIG. 3, at the bottom of the threaded portion 16, a tip 22 may be configured to be self-tapping. Referring to FIG. 4, the pedicle screw 10 may be cannulated, as shown by the passage 24 extending the length of the pedicle screw 10, with an opening at both the proximal end and the distal end of the pedicle screw 10.

Referring back to FIG. 2, prior to adding the coupling mechanism 14 and fixation rod 12, the pedicle screw 10 is first installed into the vertebra by screwing the pedicle screw 10 into place, with the use of the self-tapping configuration of pedicle screw 10 or other installation methods known in the art. Recess 20 may be used as the engagement point for drilling the pedicle screw 10 into the chosen vertebra.

Figure 5:
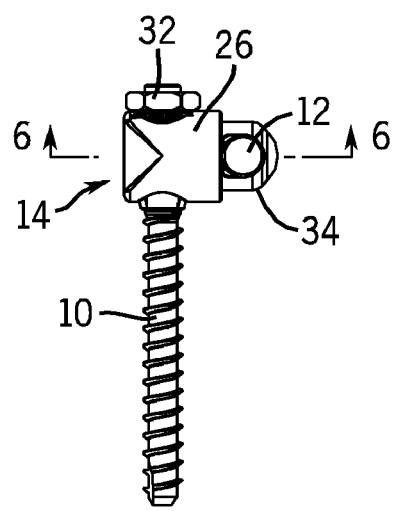
FIG. 5 is a side elevation view of the spinal fixation system of FIG. 2.
Figure 6:
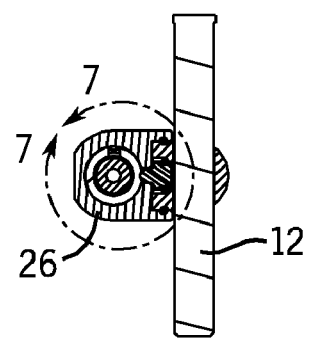
FIG. 6 is a sectional view of the spinal fixation system of FIG. 2 taken generally along line 6-6 of FIG. 5.
Figure 7:
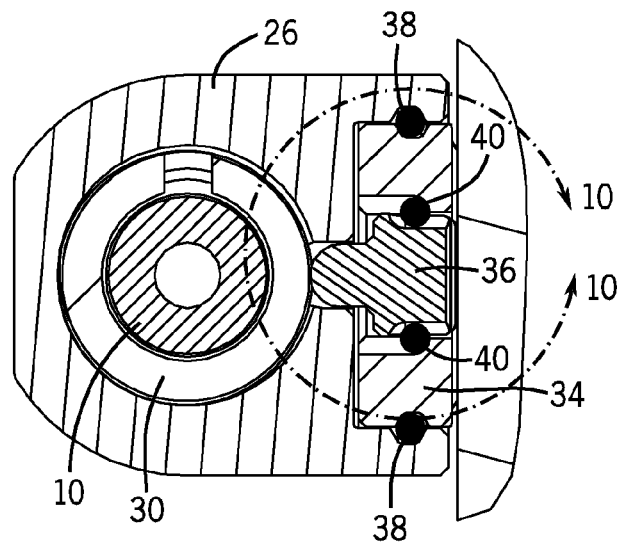
FIG. 7 is an enlarged portion of the sectional view of FIG. 6 as generally defined by line 7-7 of FIG. 6.

Further referring to FIG. 2, the coupling mechanism 14 includes a body 26, a bone screw securing device, shown as collet 28, an engagement or fastening device, shown as split ring 30, and a fastening mechanism, shown as nut 32. Referring to FIGS. 5-7, the body 26 includes a passage sized to receive the pedicle screw 10 and another passage sized to receive a fixation rod holder, shown as rod holder 34, a fixation rod securing device, shown as pin 36, ball bearings 38 and anti-spin balls 40. While the two passages extend orthogonally to one another, the two passages may extend in other directions relative to one another in other embodiments of the invention. The two passages are connected by an aperture allowing the split ring 30 to act upon the pin 36 to secure the fixation rod 12 to the pedicle screw 10. In other embodiments, the split ring 30 may be replaced by a cam, sliding pin, or a nut with a pin engagement structure.

Figure 8:
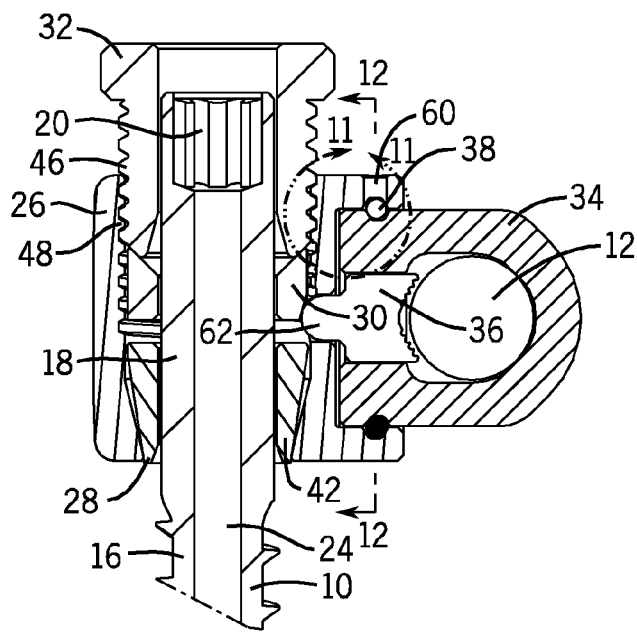
FIG. 8 is a enlarged portion of the sectional view of FIG. 4 as generally defined by line 8-8 of FIG. 4.
Figure 9:
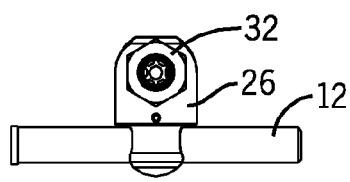
FIG. 9 is a top view of the spinal fixation system of FIG. 2.

Referring back to FIG. 2, the collet 28 includes an internal aperture designed to be fitted over post 18 and a set of compressible arms 42 designed to engage the pedicle screw 10. The split ring 30 includes an exterior groove 44 configured to mate with a semi-spherical end 62 of the pin 36. Referring to FIGS. 8 and 9, the nut 32 includes external threads 46 configured to mate with internal threads 48 on the body 26 and an engagement design 50 at the top of the nut 32 may be engaged by a tightening tool, such as a wrench having an interlocking design, that may be used to rotate the nut 32 to utilize the coupling mechanism 14 to couple the fixation rod 12 to the pedicle screw 10.

Figure 10:
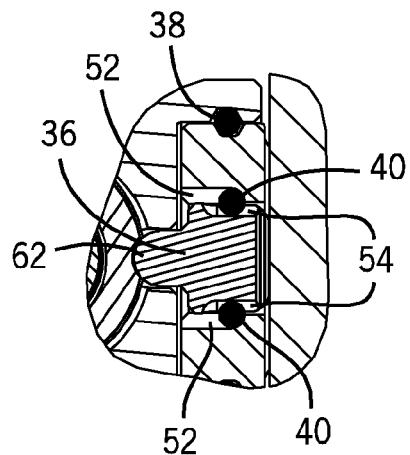
FIG. 10 is an enlarged portion of the sectional view of FIG. 7 as generally defined by line 10-10.
Figure 11:
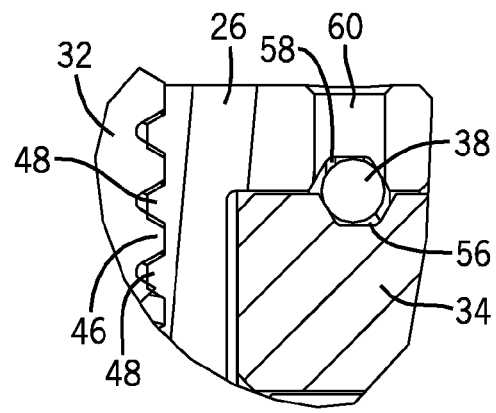
FIG. 11 is an enlarged portion of the sectional view of FIG. 8 as generally defined by line 11-11.
Figure 12:
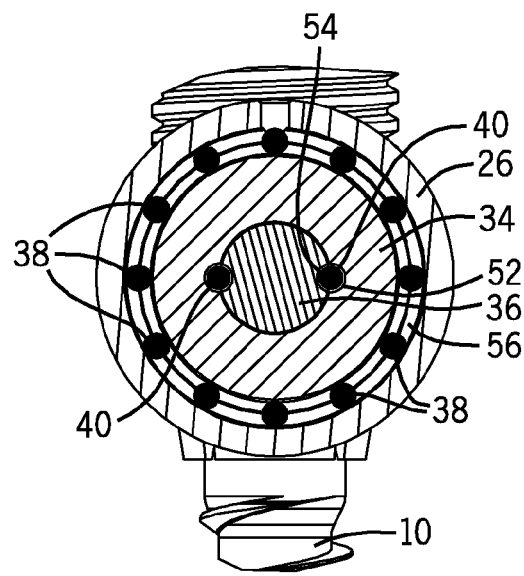
FIG. 12 is an partial sectional view of the spinal fixation system of FIG. 2 taken generally along line 12-12 of FIG. 8.

Further referring to FIG. 8, the rod holder 34 has two passages, one sized to receive the fixation rod 12 and the other sized to receive the pin 36. Referring to FIGS. 10 and 11, the rod holder 34 also has two grooves, an axial internal groove 52 that aligns with an external groove 54 on the pin 36 and a circumferential external groove 56 that aligns with an internal groove 58 on the body 26. Anti-spin balls 40 are inserted into the first pair of grooves 52, 54 to prevent the pin 36 from rotating freely with respect to the rod holder 34. However, referring to FIG. 11, the anti-spin balls 40 permit the pin 36 to be slidably coupled to the rod holder 34. Ball bearings 38 (e.g. titanium ball bearings) are inserted into the second pair of grooves 56, 58 through a ball bearing hole 60 in the body. According to an alternative embodiment, external groove 56 may be replaced with a plurality of discreet holes. Once the ball bearings 38 are in place, the ball bearing hole 60 is closed by a method known in the art (e.g. laser weld, set screw, plug) to maintain the ball bearings 38 in place. Referring to FIG. 12, the design and arrangement of the circumferential external groove 56 on the rod holder 34, the internal groove 58 on the body 26, and the ball bearings 38 allow the rod holder 34 to be rotationally coupled to the body 26.

Referring to back FIG. 2, in order to utilize the coupling mechanism 14 to couple the fixation rod 12 to the pedicle screw 10, the collet 28, split ring 30, and body 26 are placed over the post 18 after installation of the pedicle screw 10 into the chosen vertebra. The various components of the coupling mechanism 14 are slidable with respect to the fixation rod 12 and the post 18 prior to tightening to allow for proper adjustment of the various components. Once the desired placement is achieved, the nut 32 may be rotationally secured to the body 26.

Further referring to FIG. 2, the nut 32 acts as a fastening device by performing two functions. First, rotation of the nut 32 into the body 26 forces the compressible arms 42 of the collet 28 onto the post 18, thus securing the pedicle screw 10 to the body 26. Second, the rotation of the nut forces the peripheral surface of the split ring 30 outward such that the split ring 30 engages and forces the pin 36 against the fixation rod 12, thus securing the fixation rod 12 with respect to the body 26.

Referring to FIGS. 13-24, a spinal fixation system according to another embodiment of the invention includes a bone coupling element, shown as pedicle screw 110, a linking device or fixation element, shown as fixation rod 112, and a coupling mechanism 114. Referring to FIG. 13, the pedicle screw 110 is coupled to the fixation rod 112 via the coupling mechanism 114. In use, the pedicle screw 110 may be inserted through a pedicle and into a vertebra and linked to other pedicle screws by the fixation rod 112. The length of the fixation rod 112 is chosen to accommodate the total distance along the pedicle screws that are linked together.

Further referring to FIG. 13, the pedicle screw 110 includes a threaded portion 116 and a non-threaded upper portion, shown as post 118. At the top of the post 118, an engagement mechanism for a screwdriver or power drill, shown as recess 120, may be utilized. Referring to FIGS. 14 and 15, at the bottom of the threaded portion 116, a tip 122 may be configured to be self-tapping. The pedicle screw 110 may be cannulated, as shown by the passage 124 extending the length of the pedicle screw 110, with an opening at both the proximal end and the distal end of the pedicle screw 110.

Referring back to FIG. 13, prior to adding the coupling mechanism 114 and fixation rod 112, the pedicle screw 110 is first installed into the vertebra by screwing the pedicle screw 110 into place, with the use of the self-tapping configuration of pedicle screw 110 or other installation methods known in the art. Recess 120 may be used as the engagement point for drilling the pedicle screw 110 into the chosen vertebra.

Figure 17:
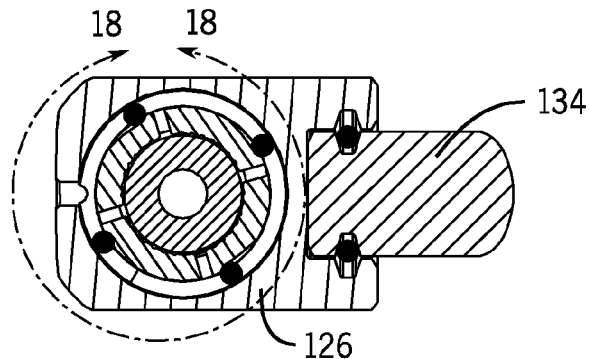
FIG. 17 is a sectional view of the spinal fixation system of FIG. 13 taken generally along line 17-17 of FIG. 16.
Figure 18:
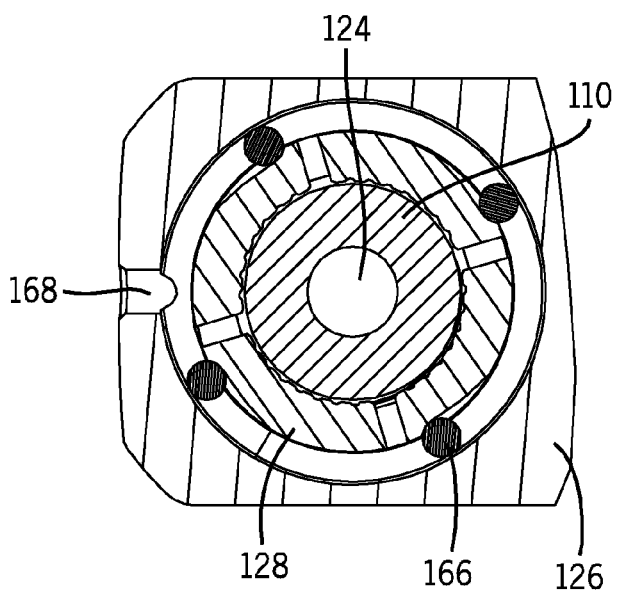
FIG. 18 is an enlarged portion of the sectional view of FIG. 17 as generally defined by line 18-18.

Referring to FIGS. 16-18, the coupling mechanism 114 includes a body 126, a bone screw securing device, shown as collet 128, which also serves as the fastening mechanism, and collet ball bearings 166. The collet ball bearings 166 are inserted into collet ball hole 168 during assembly to retain the collet 128 within the body 126. The collet ball hole 168 is closed by a method known in the art (e.g. laser weld, set screw, plug) to keep the collet ball bearings 166 in place.

Figure 19:
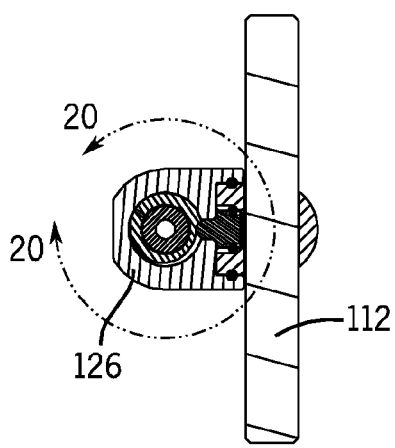
FIG. 19 is a sectional view of the spinal fixation system of FIG. 13 taken generally along line 19-19 of FIG. 16.
Figure 20:
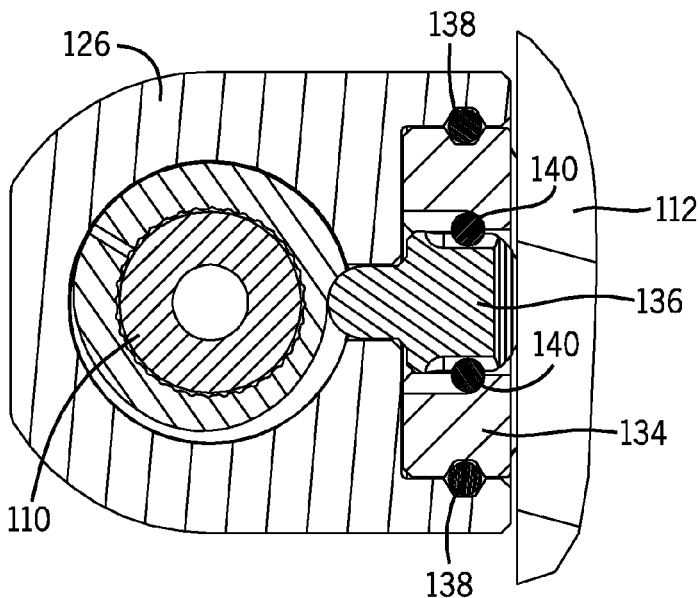
FIG. 20 is an enlarged portion of the sectional view of FIG. 19 as generally defined by line 20-20.

Referring to FIGS. 19-20, the body 126 includes a passage sized to receive the pedicle screw 110 and another passage sized to receive a fixation rod holder, shown as rod holder 134, a fixation rod securing device, shown as pin 136, ball bearings 138 and anti-spin balls 140. While the two passages extend orthogonally to one another, the two passages may extend in other directions relative to one another in other embodiments of the invention. The two passages are connected by an aperture allowing the collet 128 to act upon the pin 136 to secure the fixation rod 112 to the pedicle screw 110.

Referring back to FIG. 13, the collet 128 includes an internal aperture designed to be fitted over post 118 and a set of compressible arms 142 designed to engage the pedicle screw 110. The collet 128 includes a cam groove 144 configured to mate with a semi-spherical end 162, shown in FIG. 21, of the pin 136. The collet 128 includes an engagement design 150 at the top of the collet 128 that may be engaged by a tightening tool, such as a wrench, that may be used to rotate the collet 128 to utilize the coupling mechanism 114 to rotationally couple the fixation rod 112 to the pedicle screw 10.

Figure 21:
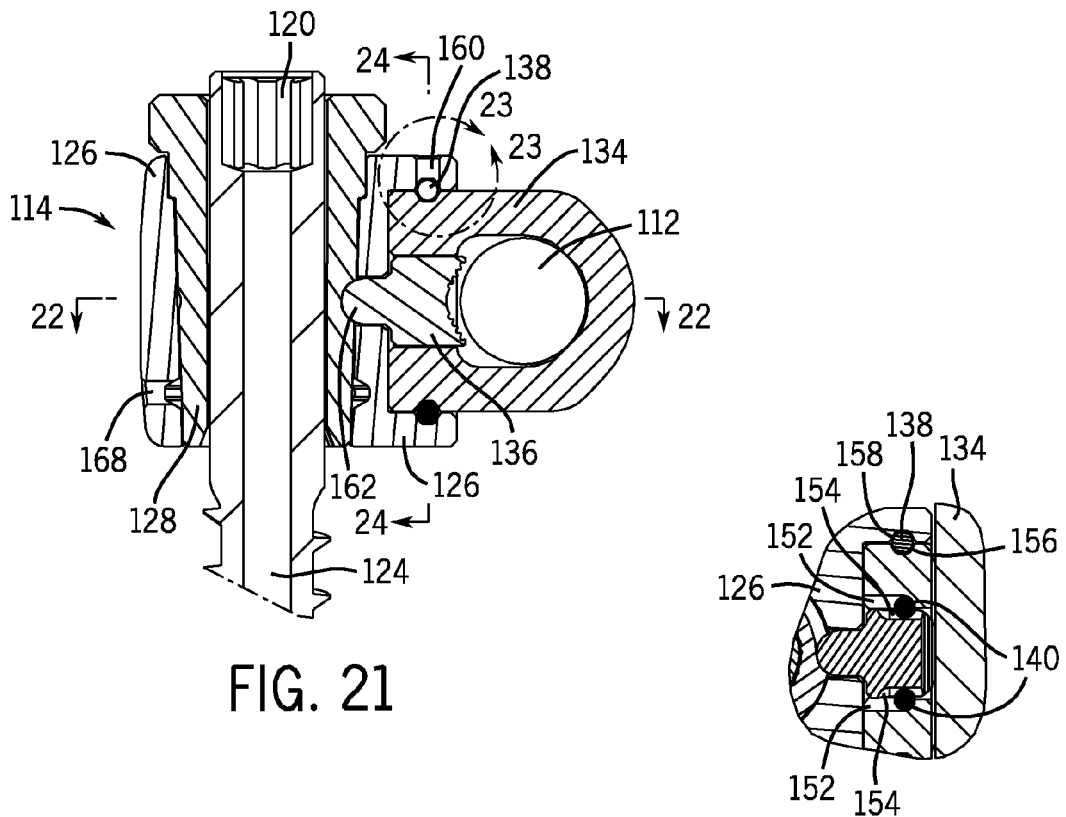
FIG. 21 is an enlarged portion of the sectional view of FIG. 15 as generally defined by line 21-21.
Figure 22:
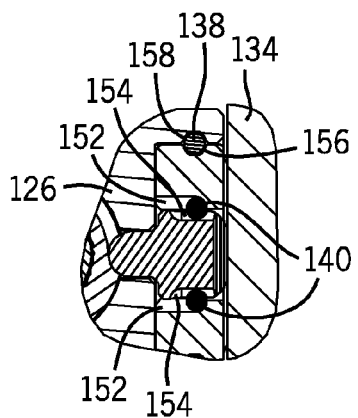
FIG. 22 is a partial sectional view of the spinal fixation system of FIG. 13 taken generally along line 22-22 of FIG. 21.
Figure 23:
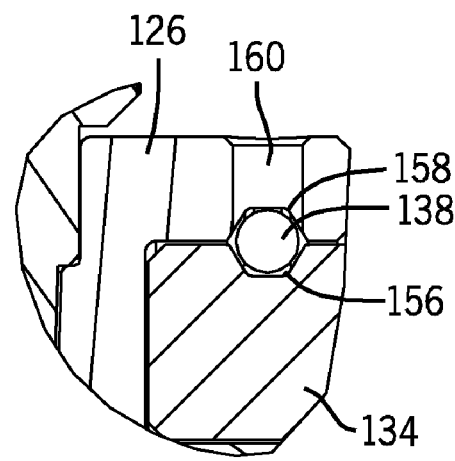
FIG. 23 is an enlarged portion of the sectional view of FIG. 21 as generally defined by line 23-23.
Figure 24:
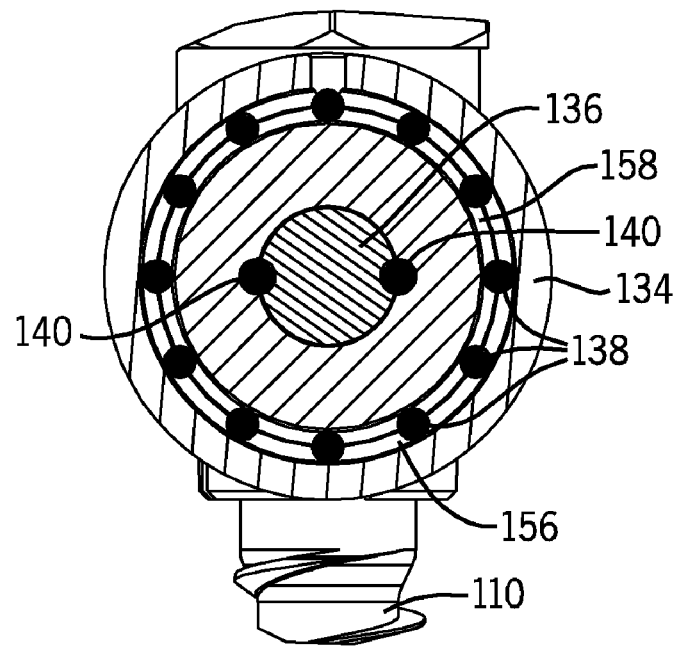
FIG. 24 is a partial sectional view of the spinal fixation system of FIG. 13 taken generally along line 24-24 of FIG. 21.
Figure 25:
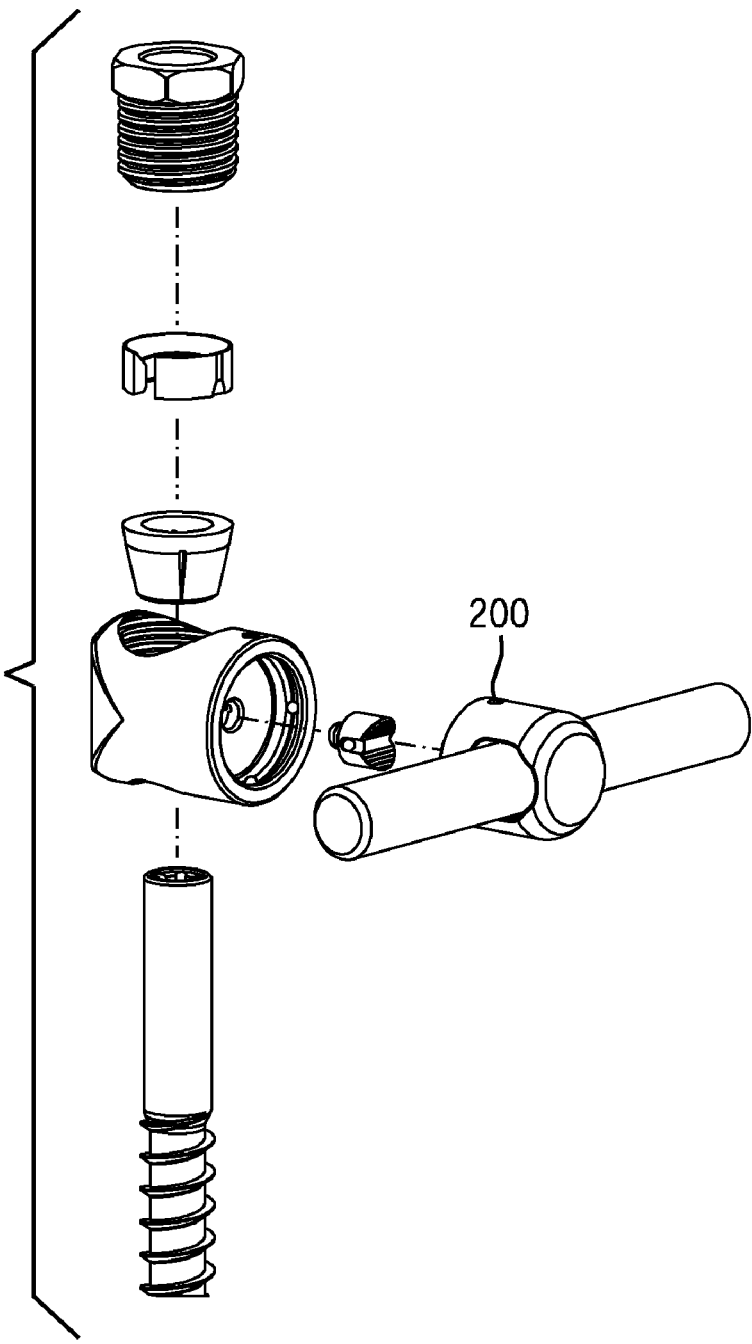
FIG. 25 is a partial exploded perspective view of a spinal fixation system according to a third embodiment of the invention.

Referring to FIG. 21, the rod holder 134 has two passages, one sized to receive the fixation rod 112 and the other sized to receive the pin 136. Additionally, referring to FIGS. 22 and 23, the rod holder 134 has two grooves: an axial internal groove 152 that aligns with an external groove 154 on the pin 136 and a circumferential external groove 156 that aligns with an internal groove 158 on the body 126. Referring to FIG. 24, anti-spin balls 140 are inserted into the first pair of grooves 152, 154 to prevent the pin 136 from rotating freely with respect to the rod holder 134; however, the anti-spin balls 140 permit the pin 136 to be slidably coupled to the rod holder 134. Referring back to FIG. 23, ball bearings 138 (e.g. titanium ball bearings) are inserted into the second pair of grooves 156, 158 through a ball bearing hole 160 in the body. Once the ball bearings 138 are in place, the ball bearing hole 160 is closed by a method known in the art (e.g. laser weld, set screw, plug) to maintain the ball bearings 138 in place. Referring back to FIG. 24, the design and arrangement of the circumferential external groove 156 on the rod holder 134, the internal groove 158 on the body 126, and the ball bearings 138 allow the rod holder 34 to be rotationally coupled to the body 126.

Referring back to FIG. 13, in order to utilize the coupling mechanism 114 to couple the fixation rod 112 to the pedicle screw 110, the collet 128 and body 126 are placed over the post 118 after installation of the pedicle screw 110 into the chosen vertebra. The various components of the coupling mechanism 114 are slidable with respect to the fixation rod 112 and the post 118 prior to tightening to allow for proper adjustment of the various components. The collet 128 may be rotated to secure the fixation rod 112 to the pedicle screw 110 via the coupling mechanism 114.

Further referring to FIG. 13, the collet 128 acts as a fastening device by performing two functions. First, rotation of the collet 128 results in the collet ball bearings 166 rolling in the camlets 164 to compress the compressible arms 142 of the collet 128 onto the post 118, thus securing the pedicle screw 110 to the body 126. Second, rotation of the collet 128 in the clockwise direction causes the cam groove 144 to act upon the pin 136 to secure the fixation rod 112 with respect to the body 126. Note that prior to installation of the rod 112, the collet 128 is configured to free spin in the counterclockwise direction. After the rod 112 has been installed and locked to the body 126, the collet 128 may be rotated in the counterclockwise direction (e.g. 45 degrees) to loosen the connection between the pin 136 and the rod 112.

Figure 26:
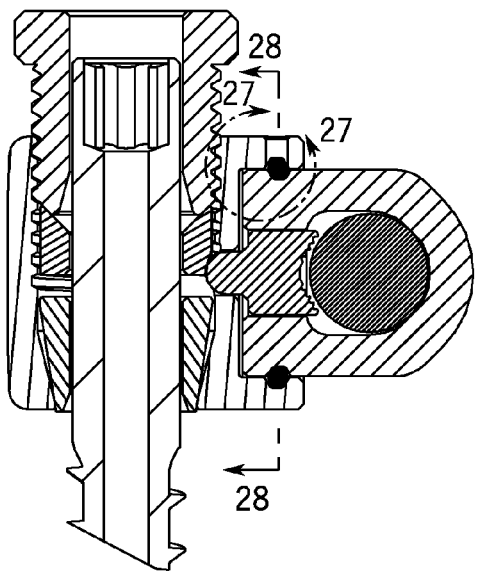
FIG. 26 is partial sectional view of the spinal fixation system of FIG. 25.
Figure 27:
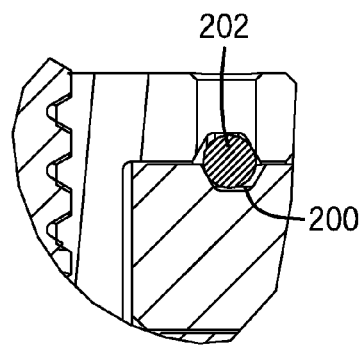
FIG. 27 is an enlarged portion of the sectional view of FIG. 26 as generally defined by line 27-27.
Figure 28:
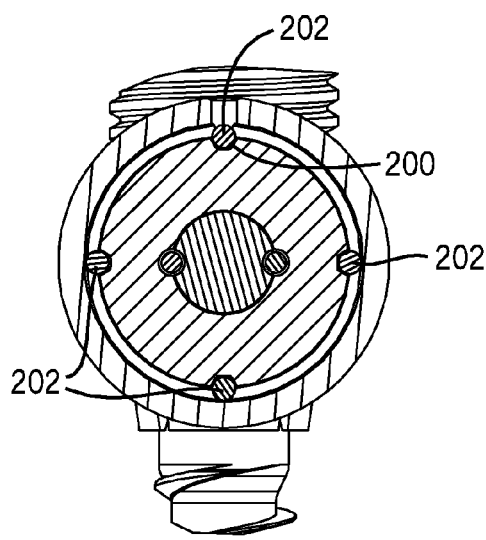
FIG. 28 is a partial sectional view of the spinal fixation system of FIG. 25 taken generally along line 28-28 of FIG. 26.
Figure 29:
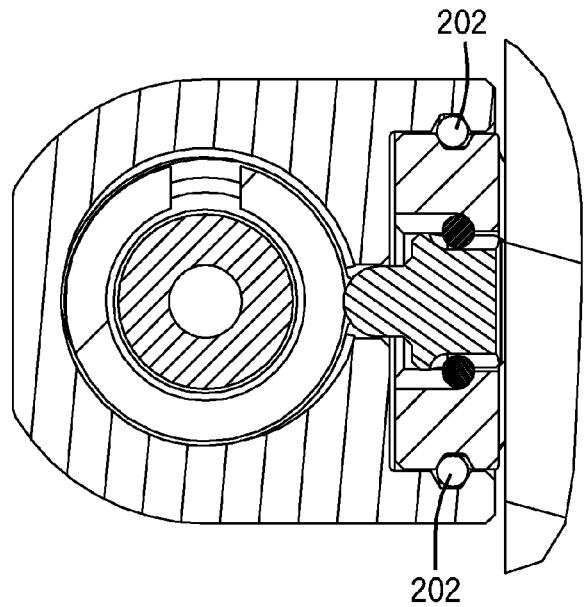
FIG. 29 is an enlarged partial sectional view of an assembled FIG. 25.

Referring to FIGS. 25-29, a spinal fixation system according to another exemplary embodiment of the invention is similar to that depicted in FIGS. 2-12 with the exception of a modified rod holder and associated ball bearings 202. FIG. 26 is a view analogous to the view of FIG. 8 and FIG. 29 is analogous to the view of FIG. 7. The rod holder may be constructed with discreet holes 200 rather than the groove 56 (compare FIG. 2 to FIG. 25). Referring to FIGS. 26-29, four ball bearings 202 permit rotation of the rod holder relative to the body (compare FIGS. 11 and 12 to FIGS. 27 and 28).

Figure 30:
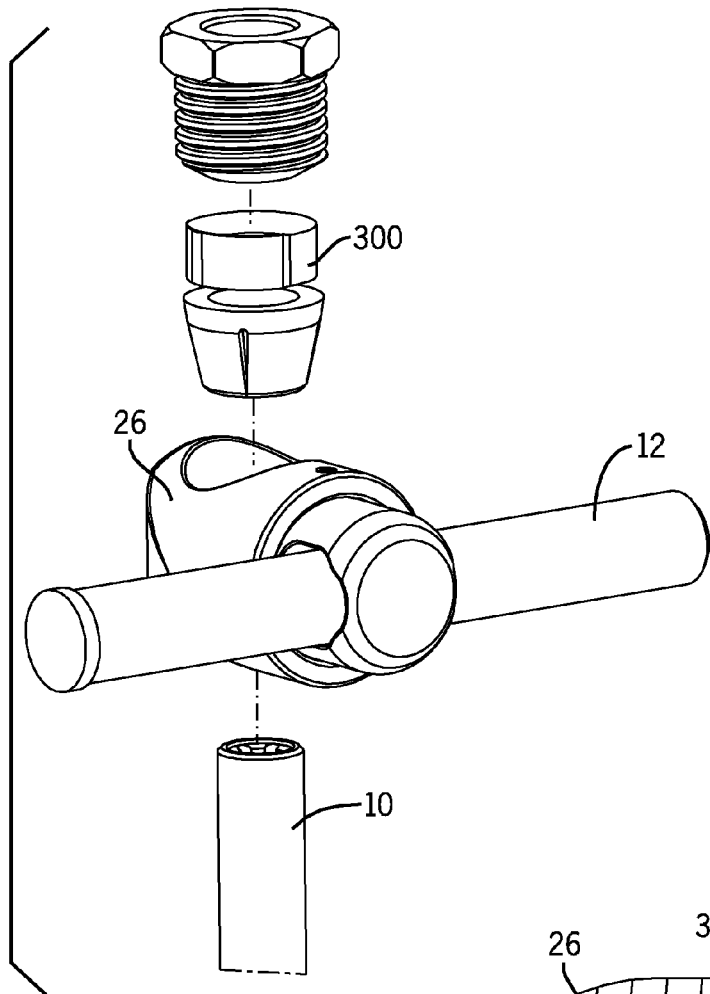
FIG. 30 is a partial exploded perspective view of a spinal fixation system according to a forth embodiment of the invention.
Figure 31:
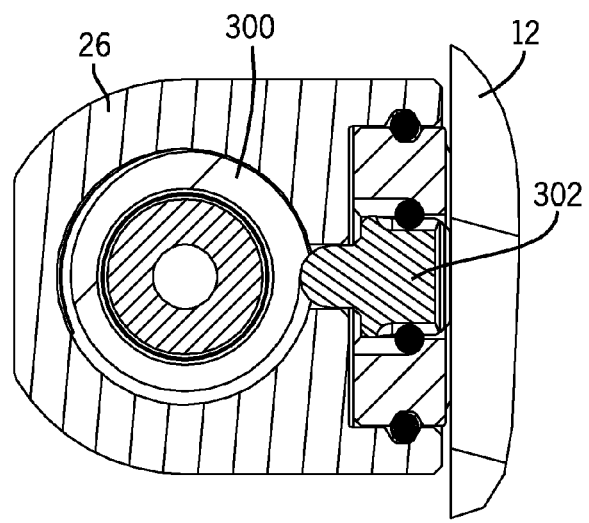
FIG. 31 is a partial sectional view of the spinal fixation system of FIG. 30.

Referring to FIGS. 30 and 31, a spinal fixation system according to another embodiment of the invention is similar to that shown in FIGS. 2-12 with the exception that a cam 300 is utilized instead of the split ring 30 (compare FIG. 2 to FIG. 30). Referring to FIG. 31 a view analogous to the view of FIG. 7, the cam 300 is configured to rotate as the nut is rotated to push pin 302 against rod 12 to secure the rod 12 to the body 26.

Referring to FIGS. 32-36, a spinal fixation system according to another embodiment of the invention is similar to that depicted in FIGS. 2-12 with the exception that the ball bearings 38 and anti-spin balls 40 have been replaced by other components. Specifically, the ball bearings 38 are replaced a retaining split ring 400 that resides within a corresponding groove 402 in the rod holder 34. Upon rotationally securing the nut 32, the collet 28 is driven into the body 26 to secure the collet 28 against the pedicle screw 10.

Figure 32:
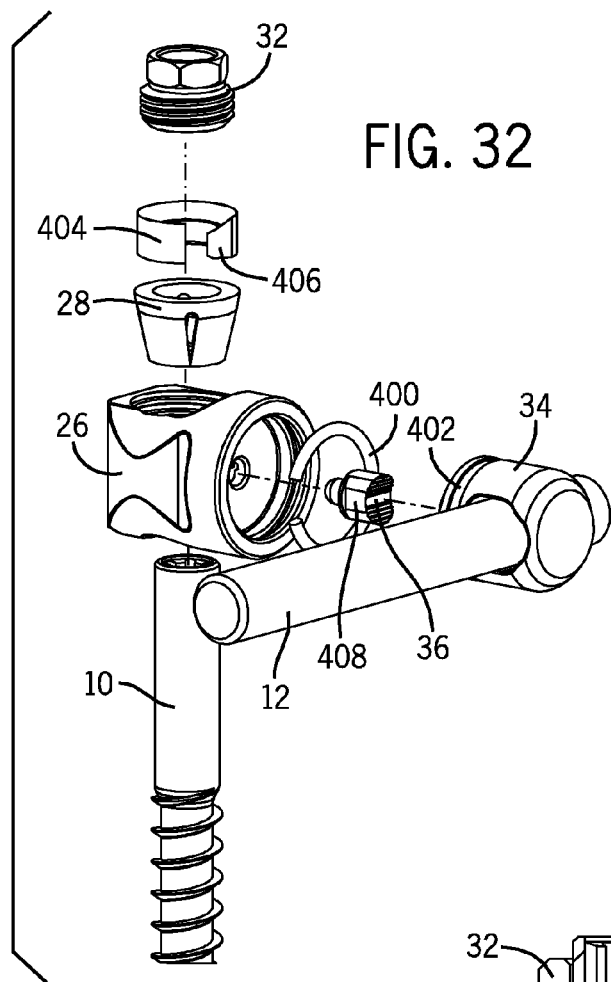
FIG. 32 is a partial exploded perspective view of a spinal fixation system according to a fifth embodiment of the invention.
Figure 33:
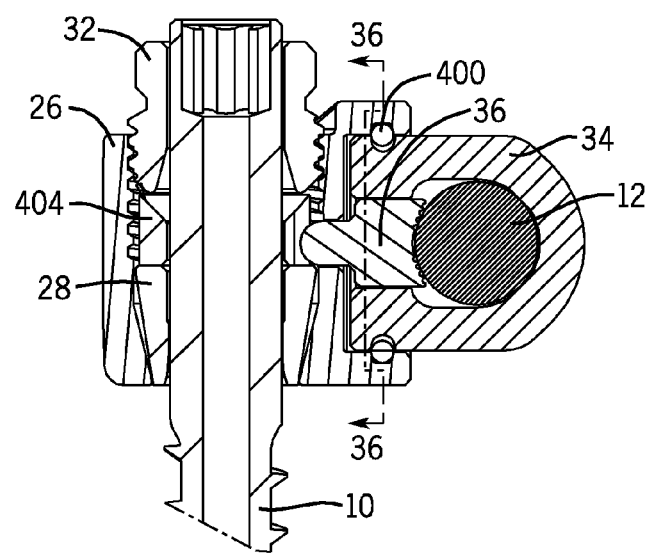
FIG. 33 is a partial sectional view of the spinal fixation system of FIG. 32.
Figure 34:
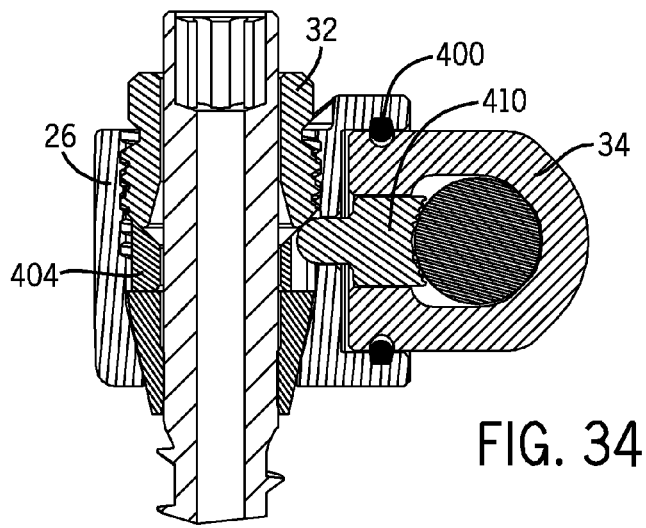
FIG. 34 is a partial sectional view of the spinal fixation system of FIG. 32.
Figure 35:
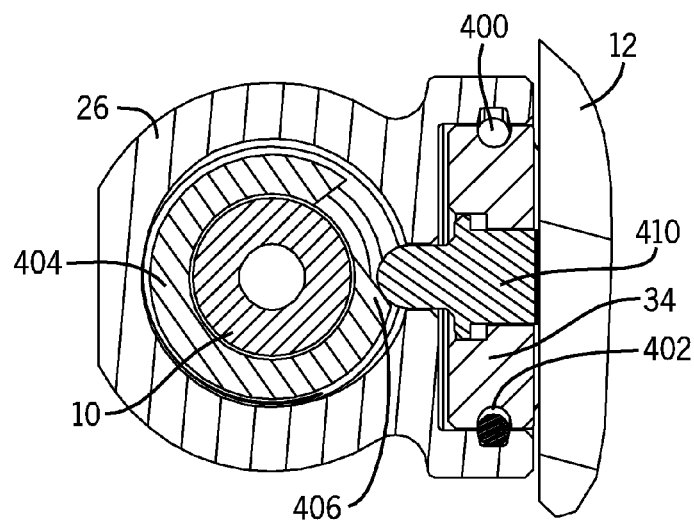
FIG. 35 is a partial sectional view of the spinal fixation system of FIG. 32.

Further referring FIG. 32, the split ring 404 located between the nut 32 and collet 28 includes an angled portion 406 that is configured to function as a cam surface to drive a pin 410 into the rod 12 upon rotation of the split ring 404. Referring to FIGS. 33-35, the split ring 404 begins to rotate during rotation of the nut 32 when the nut contacts the split ring 404. FIGS. 33 and 34 are analogous to the view of FIG. 8, showing unlocked and locked configurations of the spinal fixation system respectively. FIG. 35 is a view analogous to the view of FIG. 7 showing the pin 410 in the locked configuration. The securing of the rod 12 also results in the rod holder 34 being shifted away from the pedicle screw 10 and body 26, thereby rotationally locking the rod holder with respect to the body. Prior to rotationally locking the rod holder 34 with respect to the body 26, the rod holder 34 may be rotated to set the rod 12 in various angular positions with respect to the body 26.

Figure 36:
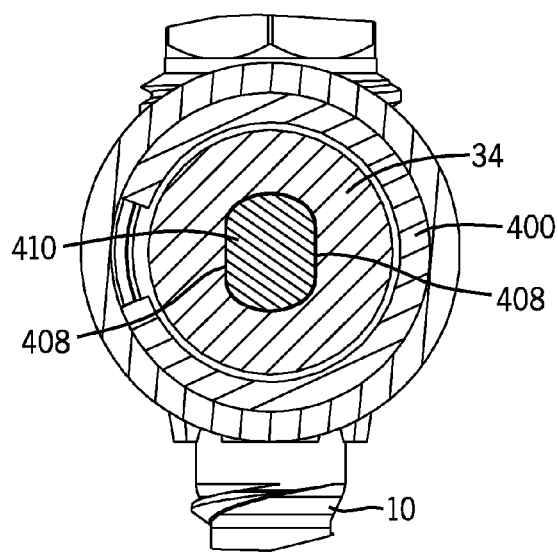
FIG. 36 is a partial sectional view of the spinal fixation system of FIG. 32 taken generally along line 36-36 of FIG. 33.

Referring to FIGS. 32 and 36, the anti-spin balls 40 (compare FIGS. 2 and 12, respectively) are replaced by pin 410 that includes anti-spin flats 408 that prevent rotation of the pin 410 with respect to the rod holder 34.

Figure 37:
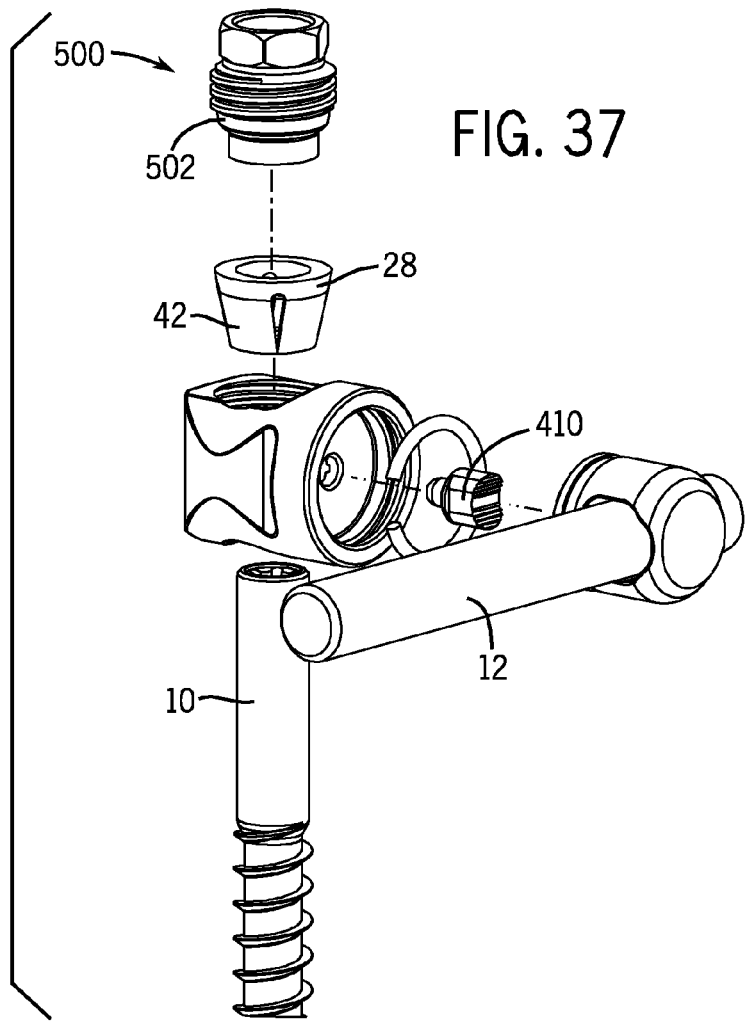
FIG. 37 is partial exploded perspective view of a spinal fixation system according to a sixth embodiment of the invention.
Figure 38:
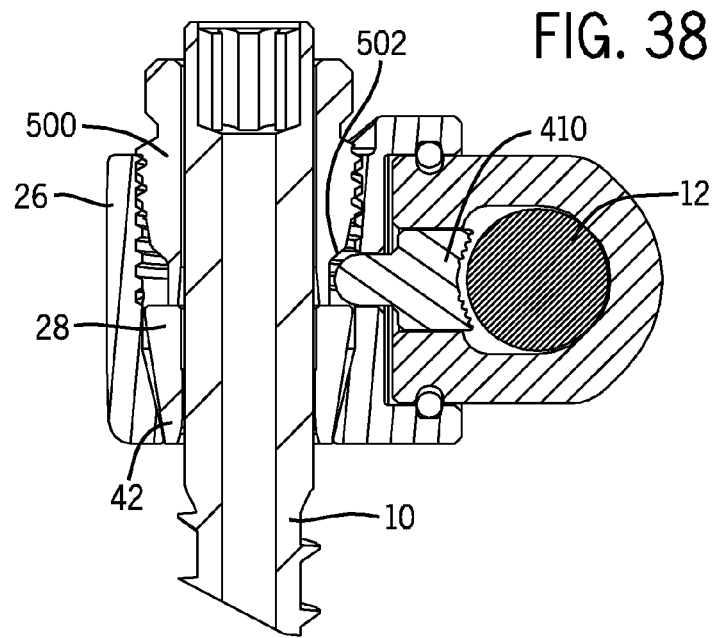
FIG. 38 is a partial sectional view of the spinal fixation system of FIG. 37.
Figure 39:
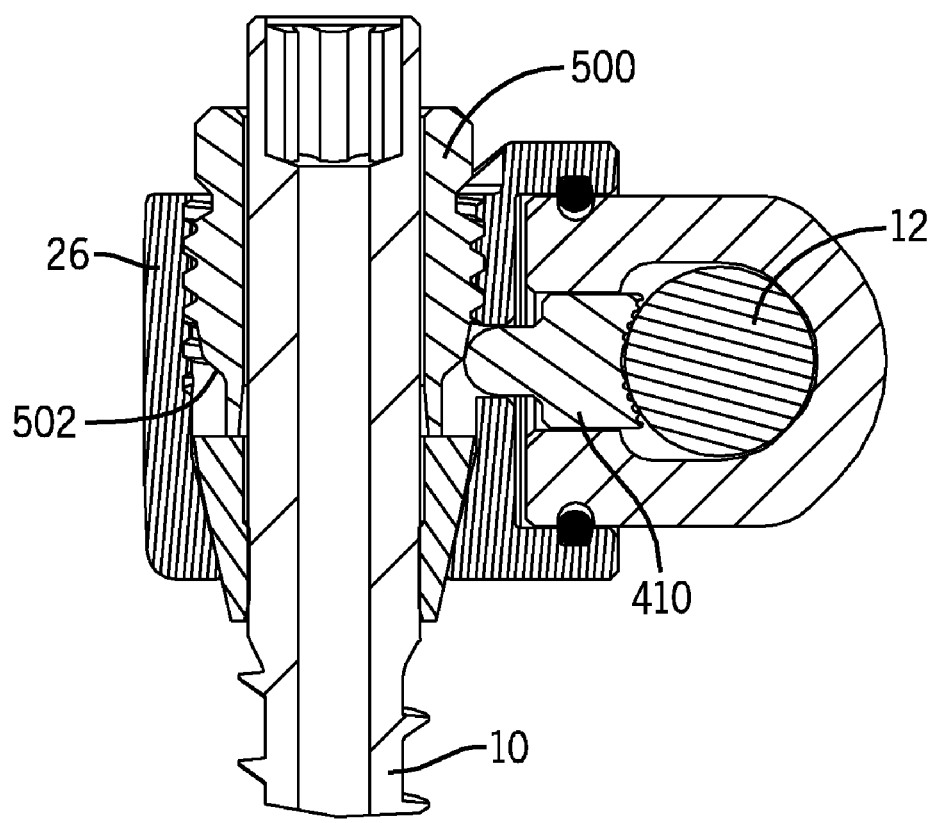
FIG. 39 is an enlarged partial sectional view of the spinal fixation system of FIG. 37.

Referring now to FIGS. 37-39, another embodiment of the invention is similar to that depicted in FIGS. 32-36 except that the fastening mechanism or nut 500 includes a pin engagement structure, shown as multi-position ramps 502. Referring to FIG. 37, the multi-position ramps 502 replace the split ring 404 (see FIG. 32). FIG. 38 is a view analogous to the view of FIG. 33 showing the system in an unlocked configuration. As the nut 500 is rotationally secured, the collet 28 is first driven downward and secured against the pedicle screw 10 as the compressible arms 42 of the collet 28 are engaged by the lower portion of the body 26. Referring to FIG. 39, a view similar to FIG. 38 with the system in a locked configuration instead, the multi-position ramps 502 are configured to engage the pin 410 to force the pin 410 against the rod 12, thereby securing the rod 12 with respect to the coupling mechanism (compare to FIGS. 34 and 35).

Figure 43:
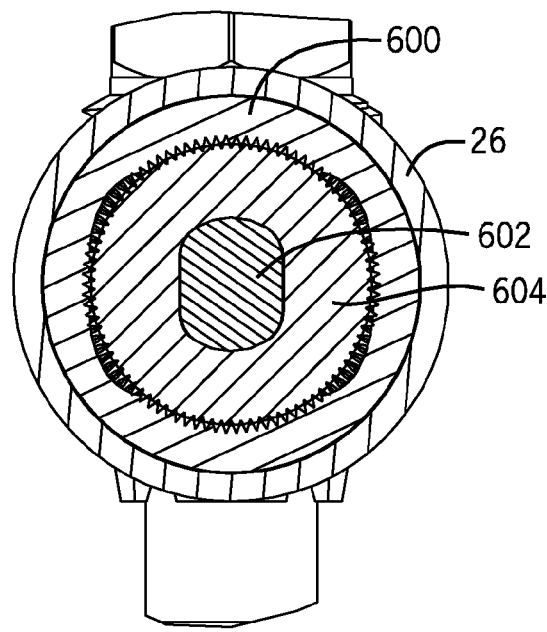
FIG. 43 is a partial sectional view of the spinal fixation system of FIG. 40.
Figure 44:
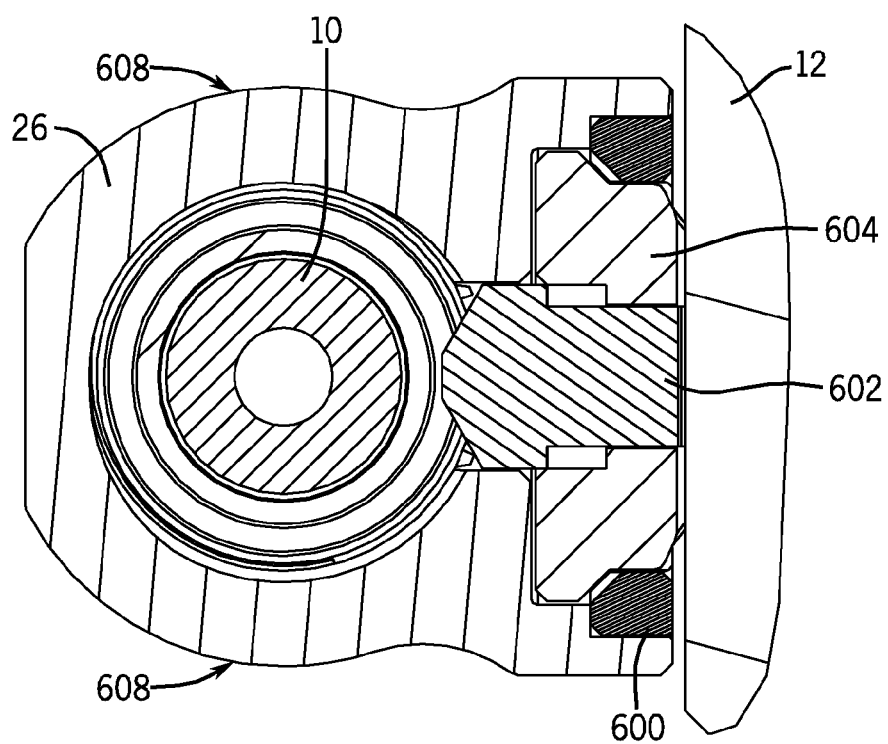
FIG. 44 is a partial sectional view of the spinal fixation system of FIG. 40.

Referring now to FIGS. 40-44, in another embodiment of the spinal fixation system similar to that depicted in FIGS. 37-39, the coupling mechanism includes a tooth-locking retaining ring 600 that allows for a tooth-locking rod holder 604 to be assembled through the diameter thereof. Referring to FIG. 41, the retaining ring 600 replaces the retaining split ring 400 (see FIG. 32). In an exemplary embodiment, the retaining ring 600 is laser welded to the body 26, although it may be secured to the body 26 in other ways known in the art. Referring to FIGS. 42 and 43, consequent the nut 500 operatively engaging the pin 602, the teeth 606 on the tooth-locking rod holder 604 engage the teeth 610 on the tooth-locking retaining ring 600 to prevent the rod holder 604 (and therefore the pin 602) from rotating freely relative to the tooth-locking retaining ring 600 (and therefore the body 26). Referring to FIG. 44, the sides 608 of the body 26 are shaped to facilitate the use of a counter-torque wrench.

The embodiments described herein share certain advantages of the inventions described in U.S. application Ser. Nos. 11/071,604 and 10/864,673. For example, referring to FIGS. 2-12, the coupling mechanism 14 is secured to both the pedicle screw 10 and fixation rod 12 by the tightening of one fastening mechanism, the nut 32. As another example, referring to FIGS. 13-24, the coupling mechanism 114 is secured to both the pedicle screw 110 and fixation rod 112 by the tightening of one fastening mechanism, the collet 128. The design is intended to simplify the process of coupling a fixation rod to a pedicle screw by reducing the number of actions necessary to accomplish the coupling task. Further, the component that is acted upon to accomplish the fastening of the coupling mechanism (e.g., the nut 32 or collet 128) is centered along the longitudinal axis of the pedicle screw 10, 110. Another advantage present in the embodiments described herein is that the coupling mechanism permits the one-step lock-up of the coupling mechanism to both the pedicle screw and the fixation rod in a configuration where the fixation rod is not located directly above the pedicle screw (i.e., the fixation rod is located lateral to the longitudinal axis of the pedicle screw).

When installing a spinal fixation system utilizing minimally invasive surgical techniques, small percutaneous apertures may be opened in the patient for installation of the individual pedicle screws. Alignment of the fastening mechanism for the coupling mechanism with the longitudinal axis of the pedicle screw allows the surgeon to more easily accomplish the attachment of the coupling mechanism. For example, when using the embodiment shown in FIGS. 2-12, the surgeon may insert a tightening instrument through the percutaneous aperture in order to rotate the nut 32 into the body 26. As another example, when using the embodiment shown in FIGS. 13-24, the surgeon may insert a tightening instrument through the percutaneous aperture in order to rotationally secure the collet 128 into the body 126. A spinal fixation system including a fastening mechanism that is substantially offset from the longitudinal axis of the pedicle screw presents additional challenges for the surgeon because the fastening mechanism may not be easily accessible through the aperture used in minimally invasive surgery.

While the detailed drawings and specific examples given herein describe various exemplary embodiments, they serve the purpose of illustration only. It is to be understood that the invention is not limited in its application to the details of construction and the arrangements of components set forth in the preceding description or illustrated in the drawings. Furthermore, other substitutions, modifications, changes, and omissions may be made in the design, operating conditions, and arrangements of the exemplary embodiments without departing from the scope of the invention as expressed in the appended claims.

What is claimed is:

1. A spinal fixation system, comprising:
    a bone screw having a longitudinal axis;
    a fixation rod configured to connect the bone screw to at least one additional bone screw, wherein the fixation rod is laterally offset relative to the longitudinal axis of the bone screw; and
    a coupling mechanism, comprising:
        a body;
        a collet at least partially received in the body and having a plurality of compressible arms configured to engage the bone screw;
        a fixation rod securing device configured to secure the coupling mechanism to the fixation rod, the fixation rod securing device comprising:
            a retaining ring secured to the body;
            a rod holder at least partially located between the retaining ring and the body and receives the fixation rod,
        wherein the retaining ring engages the rod holder to secure the rod holder to the body and to prevent the rod holder from rotating relative to the body;
        a fastening mechanism, wherein rotation of the fastening mechanism secures the collet to the bone screw and secures the rod holder to the retaining ring.

2. The spinal fixation system of claim 1, wherein the bone screw is a pedicle screw.

3. The spinal fixation system of claim 1, wherein the body comprises a first passage configured to receive the collet and the bone screw and a second passage configured to receive the fixation rod securing device.

4. The spinal fixation system of claim 1, wherein the fastening mechanism is a nut having ramps configured to operatively engage the fixation rod securing device.

5. The spinal fixation system of claim 1, further comprising a pin slidably coupled to the body and the rod holder, wherein the fastening mechanism operatively engages the pin to secure the rod holder to the fixation rod and operatively engages the collet to secure the collet to the screw.

6. The spinal fixation system of claim 5, wherein the pin includes a ramp engaged by the fastening mechanism to force the pin against the fixation rod.

7. A spinal fixation system, comprising:
    a bone screw having a longitudinal axis;
    a fixation rod configured to connect the bone screw to at least one additional bone screw, wherein the fixation rod is laterally offset relative to the longitudinal axis of the bone screw; and
    a coupling mechanism, comprising:
        a body;
        a collet at least partially received in the body and configured to secure the coupling mechanism to the bone screw, the collet having a plurality of compressible arms configured to engage the bone screw;
        a fixation rod securing device configured to secure the coupling mechanism to the fixation rod, the fixation rod securing device comprising:
            a retaining ring secured to the body;
            a rod holder at least partially located between the retaining ring and the body and receives the fixation rod, wherein the rod holder engages the retaining ring to prevent the rod holder from rotating relative to the body; and
        a fastening mechanism, wherein rotation of the fastening mechanism secures the collet to the bone screw and secures the rod holder to the retaining ring;
    wherein the retaining ring includes a plurality of teeth and the rod holder includes a plurality of teeth.

8. The spinal fixation system of claim 7, wherein the teeth on the retaining ring and the teeth on the rod holder engage to prevent rotation of the retaining ring relative to the rod holder.

9. A spinal fixation system, comprising:
    a bone screw having a longitudinal axis;
    a fixation rod configured to connect the bone screw to at least one additional bone screw, wherein the fixation rod is laterally offset relative to the longitudinal axis of the bone screw; and
    a coupling mechanism, comprising:
        a body;
        a collet at least partially received in the body and configured to secure the coupling mechanism to the bone screw, the collet having a plurality of compressible arms configured to engage the bone screw;
        a fixation rod securing device configured to secure the coupling mechanism to the fixation rod, the fixation rod securing device comprising:

a retaining ring secured to the body;

a rod holder at least partially located between the retaining ring and the body and receives the fixation rod, wherein the rod holder engages the retaining ring to prevent the rod holder from rotating relative to the body; and fastening mechanism located along the longitudinal axis of the bone screw, wherein rotation of the fastening mechanism secures the collet to the bone screw and secures the rod holder to the retaining ring.

10. A coupling mechanism for a spinal fixation system configured to couple a bone screw to a fixation rod, comprising:

a bone screw securing device configured to secure the coupling mechanism to the bone screw; and a fixation rod securing device coupling device configured to secure the coupling mechanism to the fixation rod, comprising:

a body having a first passage to receive the bone screw securing device and a second passage to receive the fixation rod securing device;

a retaining ring having a plurality of teeth facing at least partially toward the body;

a rod holder having a plurality of teeth facing at least partially away from the body and extends through an opening in the retaining ring;

a fastening mechanism, wherein rotation of the fastening mechanism secures the bone screw securing device to the bone screw and secures the rod holder to the retaining ring by engagement of the plurality of teeth on the retaining ring with the plurality of teeth on the rod holder to prevent rotation of the rod holder relative to the retaining ring a pin extending between the bone screw securing device and into the fixation rod securing device to engage the fixation rod.

11. The coupling mechanism for a spinal fixation system of claim 10, wherein the bone screw securing device is a collet.

12. The coupling mechanism for a spinal fixation system of claim 10, wherein the fastening mechanism is configured to operatively engage the bone screw securing device to secure the bone screw securing device to the bone screw.

13. The coupling mechanism for a spinal fixation system of claim 12, wherein the fastening mechanism operatively engages the fixation rod securing device to secure the fixation rod securing device to the fixation rod.

14. The coupling mechanism for a spinal fixation system of claim 13, wherein the second passage is lateral to the longitudinal axis of the bone screw.

15. The coupling mechanism for a spinal fixation system of claim 10, wherein the pin is slidable within the rod holder, wherein the fastening mechanism engages the pin to secure the rod holder to the fixation rod.

16. The coupling mechanism for a spinal fixation system of claim 10, wherein the fixation rod is laterally offset relative to a longitudinal axis of the bone screw.

* * * * *

UNITED STATES PATENT AND TRADEMARK OFFICE
CERTIFICATE OF CORRECTION

| | | |
|---|---|---|
| PATENT NO. | : 8,021,398 B2 | Page 1 of 1 |
| APPLICATION NO. | : 11/461987 | |
| DATED | : September 20, 2011 | |
| INVENTOR(S) | : Patrick J. Sweeney et al. | |

It is certified that error appears in the above-identified patent and that said Letters Patent is hereby corrected as shown below:

IN THE CLAIMS

Claim 9:
Column 11, line 7, replace "fastening mechanism located"

with --a fastening mechanism located--.

Signed and Sealed this
Eighth Day of November, 2011

David J. Kappos
*Director of the United States Patent and Trademark Office*